(12) United States Patent
Watanabe et al.

(10) Patent No.: US 10,598,608 B2
(45) Date of Patent: Mar. 24, 2020

(54) METHOD OF INSPECTING INTERIOR OF WIND TURBINE BLADE AND INSPECTION DEVICE FOR WIND TURBINE BLADE

(71) Applicant: MITSUBISHI HEAVY INDUSTRIES, LTD., Tokyo (JP)

(72) Inventors: Naota Watanabe, Tokyo (JP); Keisuke Ota, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 16/149,639

(22) Filed: Oct. 2, 2018

(65) Prior Publication Data

US 2019/0302034 A1 Oct. 3, 2019

(30) Foreign Application Priority Data

Mar. 29, 2018 (JP) .................................. 2018-064103

(51) Int. Cl.
*G01N 21/954* (2006.01)

(52) U.S. Cl.
CPC ... *G01N 21/954* (2013.01); *G01N 2021/9542* (2013.01)

(58) Field of Classification Search
CPC ..................... G01N 21/954; G01N 2021/9542
USPC ................................ 356/241.1, 237.2–237.6
See application file for complete search history.

(56) References Cited

U.S. PATENT DOCUMENTS

| | | | | |
|---|---|---|---|---|
| 2011/0182731 A1* | 7/2011 | Naka | ....................... | F03D 80/30 416/1 |
| 2012/0002038 A1 | 1/2012 | Furrer et al. | | |
| 2013/0017086 A1* | 1/2013 | Till | ......................... | F03D 17/00 416/61 |
| 2013/0061696 A1 | 3/2013 | Cabuz | | |
| 2013/0093879 A1 | 4/2013 | Bertolotti | | |
| 2013/0300855 A1* | 11/2013 | Fritz | .................... | G01N 21/954 348/82 |

(Continued)

FOREIGN PATENT DOCUMENTS

| | | |
|---|---|---|
| JP | S53-116689 A | 10/1978 |
| JP | H07-279819 A | 10/1995 |
| JP | 2013-134172 A | 7/2013 |

OTHER PUBLICATIONS

Japan Patent Office, "Office Action for Japanese Patent Application No. 2018-064103," dated Jul. 9, 2019.

(Continued)

*Primary Examiner* — Isiaka O Akanbi

(74) *Attorney, Agent, or Firm* — Manabu Kanesaka; Kenneth Berner; Benjamin Hauptman

(57) ABSTRACT

Provided is a method that enables an interior of a wind turbine blade to be safely inspected. A method of inspecting an interior of a wind turbine blade includes the steps of: placing, in the wind turbine blade, an inspection unit including a support frame, at least one wheel rotatably provided to the support frame, and inspection equipment attached to a front portion of the support frame in a traveling direction; and conveying the inspection unit from a blade root portion toward a blade tip portion of the wind turbine blade. The conveying step includes connecting at least one extension bar to a back end portion of the inspection unit, and sending the inspection unit by pushing the extension bar toward the blade tip portion.

10 Claims, 10 Drawing Sheets

(56) References Cited

U.S. PATENT DOCUMENTS

2014/0140848 A1    5/2014  Fuertes et al.
2015/0240788 A1*   8/2015  Kayama ................ G01N 19/08
                                                      416/61

OTHER PUBLICATIONS

Japan Patent Office, "Office Action for Japanese Patent Application No. 2018-064103," dated Feb. 12, 2020.

* cited by examiner

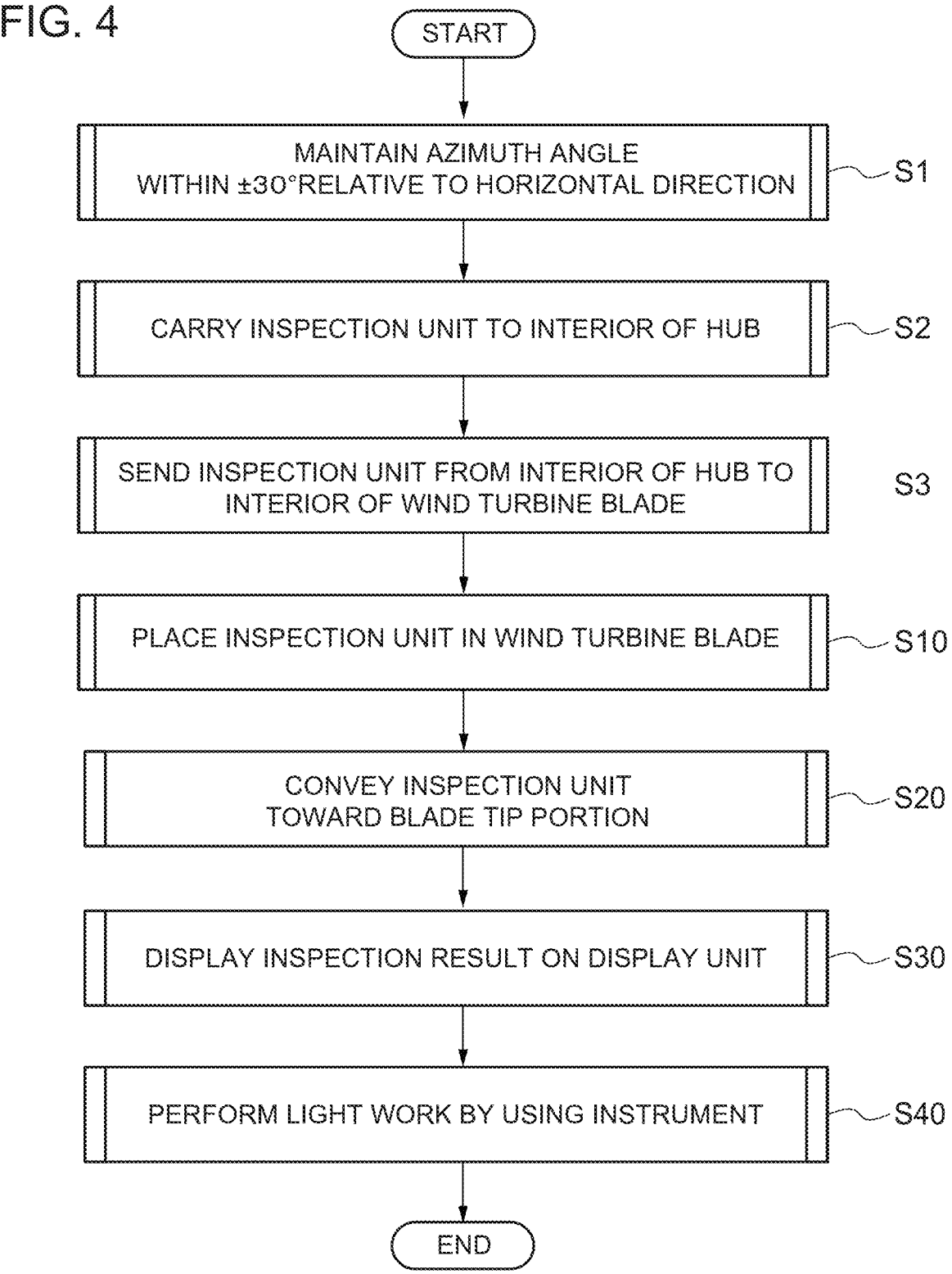

METHOD OF INSPECTING INTERIOR OF WIND TURBINE BLADE AND INSPECTION DEVICE FOR WIND TURBINE BLADE

RELATED APPLICATIONS

The present application is based on, and claims priority from, Japanese Application No. JP2018-064103 filed Mar. 29, 2018, the disclosure of which is hereby incorporated by reference herein in its entirety.

TECHNICAL FIELD

The present disclosure relates to a method of inspecting an interior of a wind turbine blade and an inspection device for a wind turbine blade.

BACKGROUND

Typically, inspection methods and inspection devices for inspecting an interior of a wind turbine blade of a wind power generation facility (hereinafter, also referred to as a wind turbine) have been known. For example, Patent Document 1 discloses a method in which a wind turbine blade serving as an inspection target is arranged so as to extend downward, that is, with an azimuth angle of 180°, a cable is suspended from a hub to an interior of the wind turbine blade, and the interior of the wind turbine blade is inspected using a camera or a sensor attached to the cable.

CITATION LIST

Patent Literature

Patent Document 1: U.S. Patent Application Publication No. 2013/0300855 (Specification)

SUMMARY

With the inspection method disclosed in Patent Document 1 described above, the interior of the wind turbine blade is inspected from a blade root side, that is, from the upper side of the wind turbine blade arranged to extend downward. Thus, the method is not free of risk of an operator or an object falling down in the wind turbine blade. The wind turbine blade may be horizontally arranged to avoid such a risk. Unfortunately, with this arrangement, the camera or the sensor attached to the cable is difficult to convey to a blade tip.

An object of at least some embodiments of the disclosure is to enable an interior of a wind turbine blade to be safely inspected.

(1) A method of inspecting an interior of a wind turbine blade according to at least one embodiment of the disclosure includes the steps of:

placing, in the wind turbine blade, an inspection unit including a support frame, at least one wheel rotatably provided to the support frame, and inspection equipment attached to a front portion of the support frame in a traveling direction; and conveying the inspection unit from a blade root portion toward a blade tip portion of the wind turbine blade.

The conveying step includes connecting at least one extension bar to a back end portion of the inspection unit, and sending the inspection unit by pushing the extension bar toward the blade tip portion.

In the method according to (1) described above, the inspection unit is placed in the wind turbine blade. The extension bar is connected to the back end portion of the inspection unit and is pushed toward the blade tip portion. Thus, the inspection unit with the wheel is sent toward the blade tip portion. In this process, the extension bar may be additionally connected in accordance with a blade length, so that the inspection unit can be conveyed to the blade tip portion. Thus, the inspection unit can be conveyed to the blade tip portion, where the operator cannot enter, in the wind turbine blade laid on the ground or an ocean or attached to the wind turbine while being horizontally or substantially horizontally arranged. All things considered, risk of an operator or an object falling down in the wind turbine blade can be avoided for example, so that the interior of the wind turbine blade can be safely inspected.

(2) In some embodiments, the method according to (1) described above may further include a step of maintaining an azimuth angle of the wind turbine blade, attached to a wind turbine, to be within ±30° relative to a horizontal direction, and the step of placing the inspection unit in the wind turbine blade and the conveying step may be performed on the wind turbine blade attached to the wind turbine with the azimuth angle maintained in the state in the maintaining step.

In the method according to (2) described above, the azimuth angle of the wind turbine blade in a state of being attached to the wind turbine is maintained to be within a range of ±30° relative to the horizontal direction, that is, 90°±30° or 270°±30°. Thus, the inspection can be performed for the interior of the wind turbine blade in the state of being attached to the wind turbine to be maintained at an angle enabling an operator to move in the wind turbine blade generally safely. Thus, the wind turbine blade needs not to be detached for the inspection, whereby an inspection cost can be reduced and the work period can be shortened.

(3) In some embodiments, in the method according to (1) or (2) described above, the conveying step may include coupling a front end portion of the extension bar to a back end portion of the inspection unit that has been sent or to a back end portion of another of the extension bars that is a rearmost extension bar.

In the method according to (3) described above, the inspection unit is conveyed toward the blade tip portion by arranging the inspection unit at the forefront, that is, on the blade tip portion side, and coupling the extension bar to the back end portion, that is, the blade root portion side of the inspection unit, or coupling the front end portion of the additional extension bar to the back end portion of another of the extension bars additionally coupled that is a rearmost extension bar. With the extension bar additionally coupled in this manner, the effect described in any one of (1) and (2) described above can be obtained with a simple configuration.

(4) In some embodiments, in the method according to any one of (1) to (3) described above, the extension bar may be configured to be extendable in a longitudinal direction, and the conveying step may include extending the extension bar in the longitudinal direction.

In the method according to (4) described above, the extendable extension bar is used that can be contracted to be more easily conveyed for inspecting the interior of the wind turbine blade, for example, so that a larger number of extension bars can be conveyed at once. Furthermore, the extension bar in the extended state may be coupled, so that the number of extension bars required for sending the inspection unit can be reduced. Furthermore, a smaller number of extension bars can be more easily conveyed for inspection with only a limited space available around the blade root portion, compared with a case where non-extendable extension bars are used. Thus, higher operability can be achieved.

(5) In some embodiments, the method according to any one of (1) to (4) described above may further include the steps of:

carrying the inspection unit to an interior of a hub to which the wind turbine blade is attached; and sending the inspection unit from the interior of the hub to the interior of the wind turbine blade.

In the method according to (5) described above, the interior of the wind turbine blade in a state of being attached to the hub of the wind turbine is inspected with the inspection unit carried to the interior of the hub on the blade root portion side, and then sent from the interior of the hub to the interior of the wind turbine blade. Thus, the effect described in any one of (1) to (4) described above can be achieved for the operation in a limited space within the hub for inspecting the interior of the wind turbine blade in the state of being attached to the wind turbine.

(6) In some embodiments, in the method according to any one of (1) to (5) described above, the extension bars may be each formed to have a length in a longitudinal direction, in a shortest state, of 3 m or less, or of twice a diameter of the blade root portion or less.

In the method according to (6) described above, the extension bars are each formed to have a length in a longitudinal direction, in a shortest state, of 3 m or less, or of twice the diameter of the blade root portion or less. Thus, the extension bars with a length suitable to be conveyed can be used for the inspection, regardless of the blade length of the wind turbine blade that is the inspection target. Furthermore, the extension bars can be smoothly carried to the interior of the hub temporarily when required, for inspecting the interior of the wind turbine blade in the state of being attached to the wind turbine, for example.

(7) In some embodiments, in the method according to any one of (1) to (6) described above, the inspection equipment may include an image capturing device capable of capturing an image of the interior of the wind turbine blade.

In the method according to (7) described above, an image of the interior of the wind turbine blade can be captured with the image capturing device serving as the inspection equipment. Thus, visual information about the interior of the wind turbine blade can be obtained to achieve more accurate inspection. For example, an image capturing device or the like featuring a wider angle of view than fiber scopes or the like may be employed as the image capturing device, so that a clearer image can be obtained to achieve even more accurate inspection.

(8) In some embodiments, in the method according to any one of (1) to (7) described above, the inspection equipment may include an illumination device capable of irradiating at least a front side in the traveling direction.

In the method according to (8) described above, at least the front side in the traveling direction can be irradiated by using the illumination device serving as the inspection equipment. Thus, for example, operability and accuracy can be improved for visual inspection performed by the operator within his or her visually recognizable range. Furthermore, for example, the image capturing device and the like can also be used as the inspection equipment in this configuration to capture an even clearer image with the image capturing device, whereby the inspection accuracy can be further improved.

(9) In some embodiments, in the method according to any one of (1) to (8) described above, the inspection unit may further include a display unit that displays an inspection result obtained by the inspection equipment, and the method may further include a step of displaying the inspection result on the display unit.

In the method according to (9) described above, the inspection result obtained by the inspection equipment is displayed on the display unit. Thus, the operator on site can recognize the inspection result in real time, whereby the interior of the wind turbine blade can be inspected with higher operability and accuracy.

(10) In some embodiments, in the method according to any one of (1) to (9) described above, the extension bars may be each provided with a graduation indicating a distance between a back end portion of the extension bar and a tip of the inspection unit, or an index indicating a coupling number of the extension bars, starting from the inspection unit, and the conveying step may include conveying the inspection unit while checking the graduation or the index.

In the method according to (10) described above, the inspection unit can be conveyed toward the blade tip portion while checking the graduation or the index provided to the extension bars. Thus, the operator can easily recognize a position of a portion in the wind turbine blade where an abnormality has been found, in a blade spanwise direction or relative to the entire wind turbine blade. The position thus recognized enables the operability of the inspection to be improved, and can contribute to decision making for taking appropriate measures for performing the repairing and the like on the wind turbine blade, for example.

(11) In some embodiments, the method according to any one of (1) to (10) described above may further include a step of performing a light work involved in an inspection, by using an instrument provided to a front end portion of the inspection unit.

In the method according to (11) described above, the light work involved in the inspection can be performed with the instrument provided to the front end portion of the inspection unit. Examples of the light work may include removal of an obstacle, chemical spraying, light/sound emission, and cutting or attaching a member. With this configuration, the inspection can be performed through an operation with a higher degree of freedom.

(12) An inspection device for a wind turbine blade according to at least one embodiment of the disclosure includes:

an inspection unit including a support frame that is long in a traveling direction, wheels rotatably provided to front and back portions of the support frame, and inspection equipment attached to the front portion of the support frame in the traveling direction; and at least one extension unit including an extension bar connected to a back end portion of the inspection unit.

In the configuration according to (12) described above, as in (1) described above, the inspection unit is placed in the wind turbine blade. The extension bar is connected to the back end portion of the inspection unit, and the extension unit including the extension bar is pushed toward the blade tip portion. Thus, the inspection unit with the wheel is sent toward the blade tip portion. In this process, the extension bar may be additionally connected in accordance with a blade length, so that the inspection unit can be conveyed to the blade tip portion. Thus, the inspection unit can be conveyed to the blade tip portion, where the operator cannot enter, in the wind turbine blade laid on the ground or an ocean or attached to the wind turbine while being horizontally or substantially horizontally arranged. All things considered, risk of an operator or an object falling down in the wind turbine blade can be avoided for example, so that the interior of the wind turbine blade can be safely inspected.

(13) In some embodiments, the configuration according to (12) described above may further include a sensor that is arranged in a periphery of the inspection equipment and that detects contact with surroundings in at least one of a height direction or a width direction.

In the configuration according to (13) described above, the sensor can detect contact between the inspection unit and surroundings in at least one of the height direction or the width direction. Thus, the for example, contact between the inspection unit and the inner surface of the wind turbine blade, a structure of the wind turbine blade, or a foreign object and the like in the wind turbine blade can be detected.

(14) In some embodiments, in the configuration according to (13) described above, the inspection unit may further include a notification unit that issues a notification indicating a detection result obtained by the sensor.

In the configuration according to (14) described above, the notification unit issues the notification indicating the detection result obtained by the sensor. Thus, the operator can recognize and record the contact between the inspection equipment and the surroundings. For example, the traveling direction of the inspection unit can be corrected, the inspection can be terminated in response to recognizing that the inspection unit has reached a portion near the blade tip portion, and other like actions can be made on the basis of the notification issued by the notification unit.

At least one embodiment of the disclosure can enable an interior of a wind turbine blade to be safely inspected.

BRIEF DESCRIPTION OF DRAWINGS

FIG. 4 is a flowchart illustrating a method of inspecting an interior of a wind turbine blade according to another embodiment;

DETAILED DESCRIPTION

Figure 1:
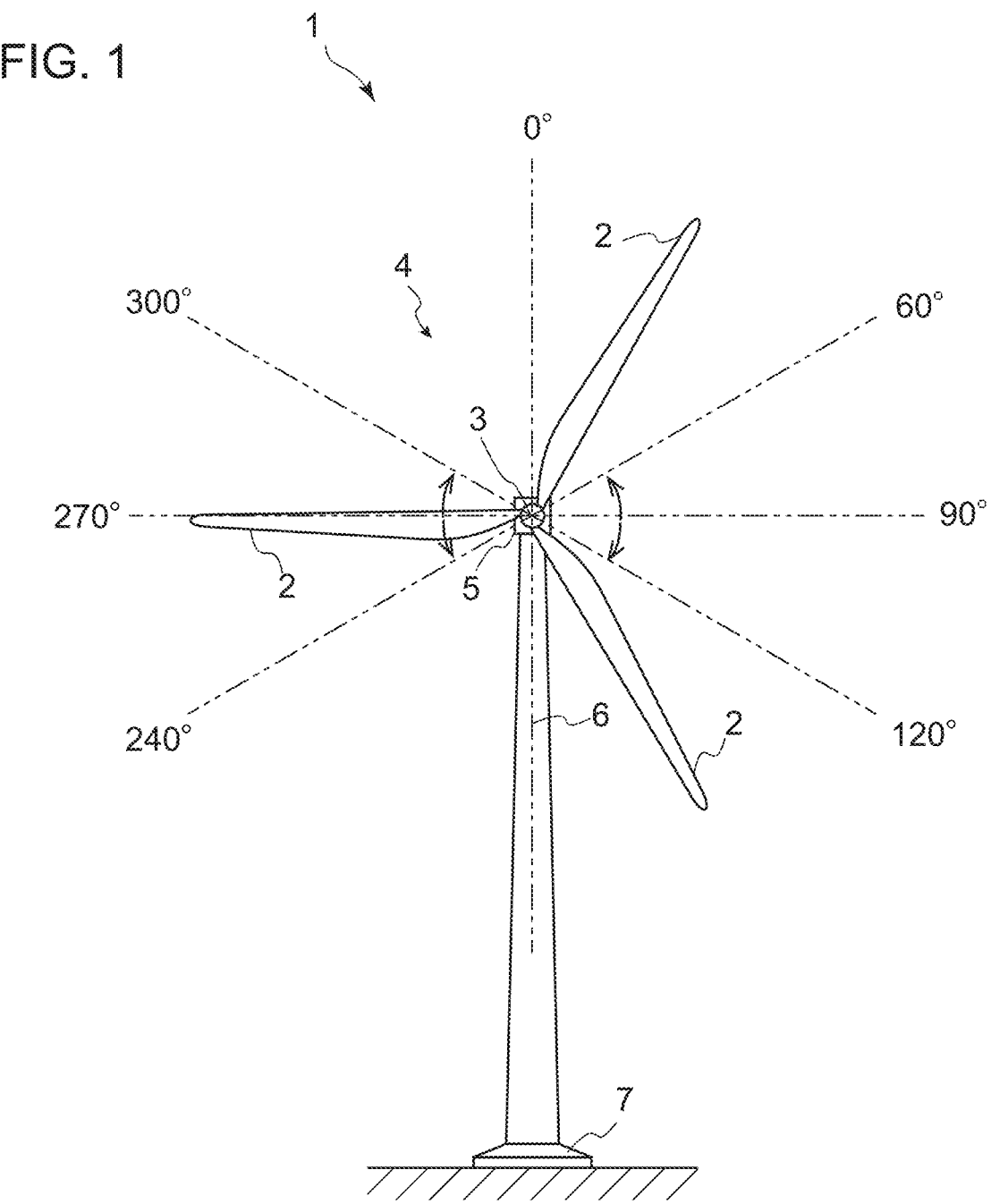
FIG. 1 is a schematic view illustrating a wind power generation facility according to one embodiment.

Some embodiments of the disclosure are described with reference to the accompanying drawings. The size, material, shape, other relative arrangements, and the like described as embodiments or illustrated in the drawings are not intended to limit the scope of the disclosure to these, and are merely illustrative.

For example, expressions that represent relative or absolute arrangements such as "in a direction", "along a direction", "parallel", "perpendicular", "center", "concentric", or "coaxial" refer not only to what exactly these expressions represent but also to states that allow tolerance or are relatively displaced by such a degree of angle or distance that can achieve the same functions.

For example, expressions that means things are in an identical state such as "same", "identical", or "homogenous" refer not only to exactly identical states but also to states that allow tolerance or include such a difference that can achieve the same functions.

For example, expressions on shapes such as rectangular or cylindrical refer not only to shapes such as rectangular or cylindrical in a geometrically exact sense but also to such shapes that include protrusions, recesses, chamfered parts, or the like as long as the same functions are available.

Expressions that represent "comprising", "including", "being provided with", "with", or "having" one component are not exclusive expressions that would exclude the existence of other component(s).

Figure 2:
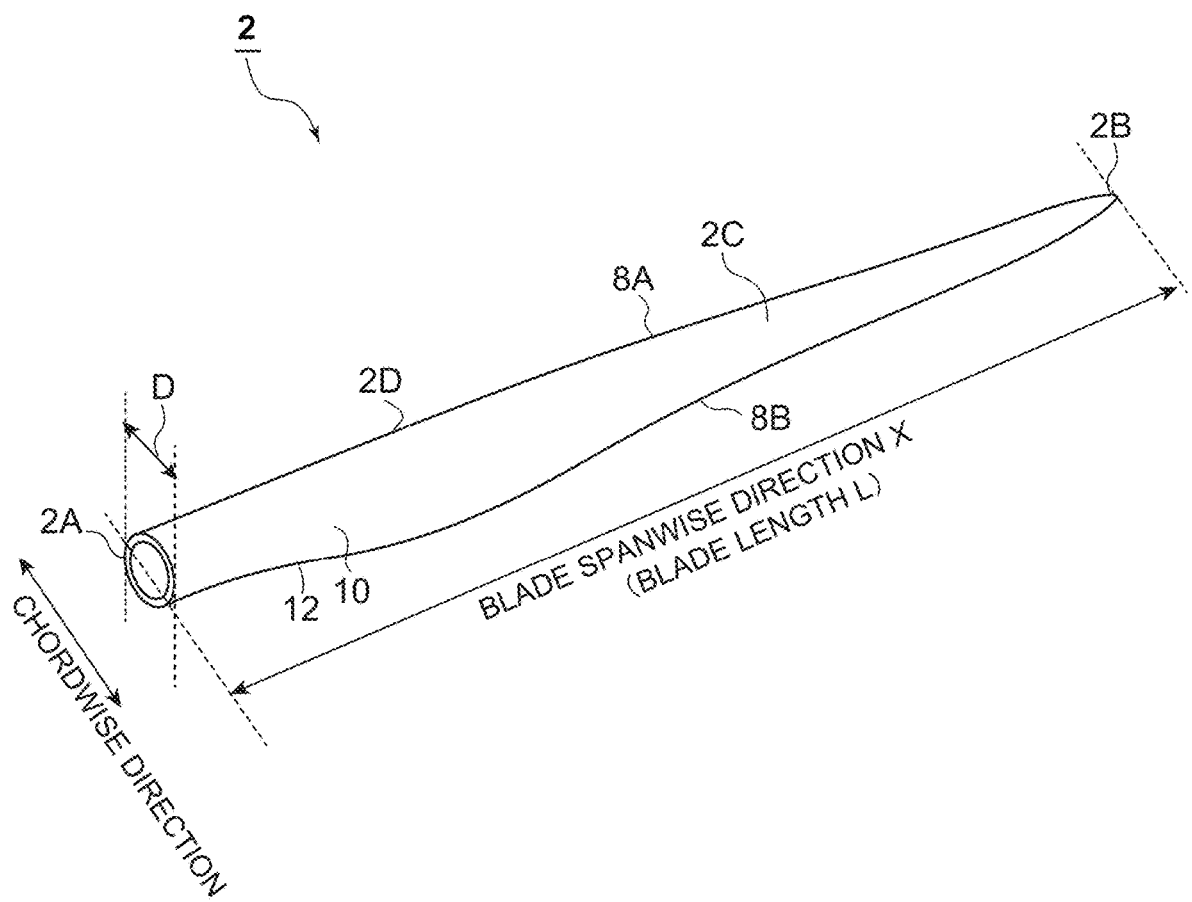
FIG. 2 is a perspective view illustrating an entire wind turbine blade according to one embodiment.
Figure 3:
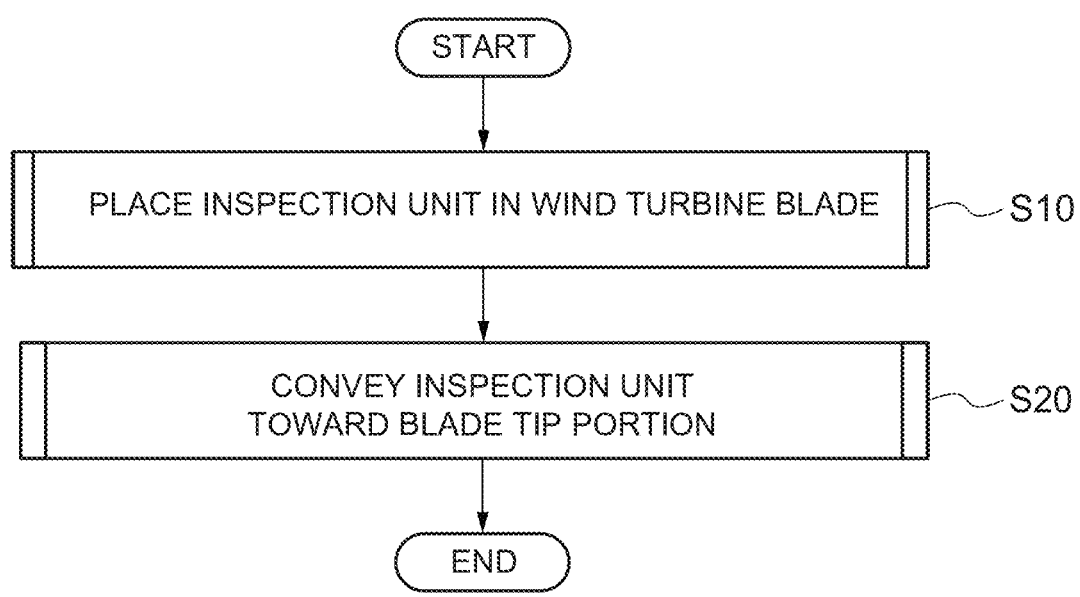
FIG. 3 is a flowchart illustrating a method of inspecting an interior of a wind turbine blade according to one embodiment.
Figure 5A:
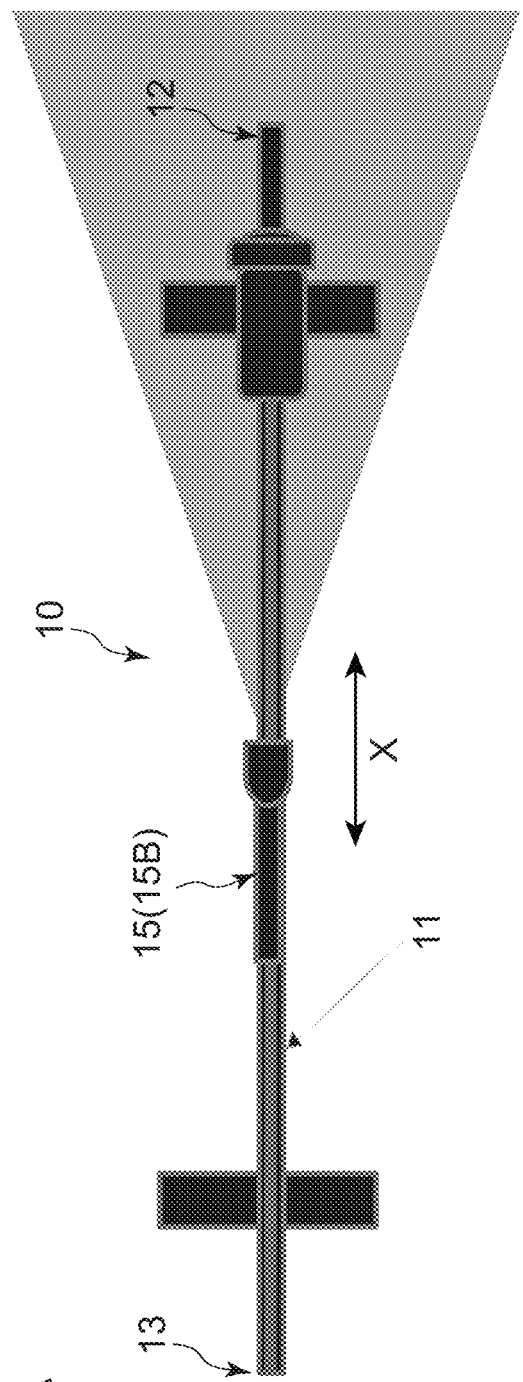
FIGS. 5A and 5B are each a schematic view illustrating an inspection unit according to one embodiment.
Figure 5B:
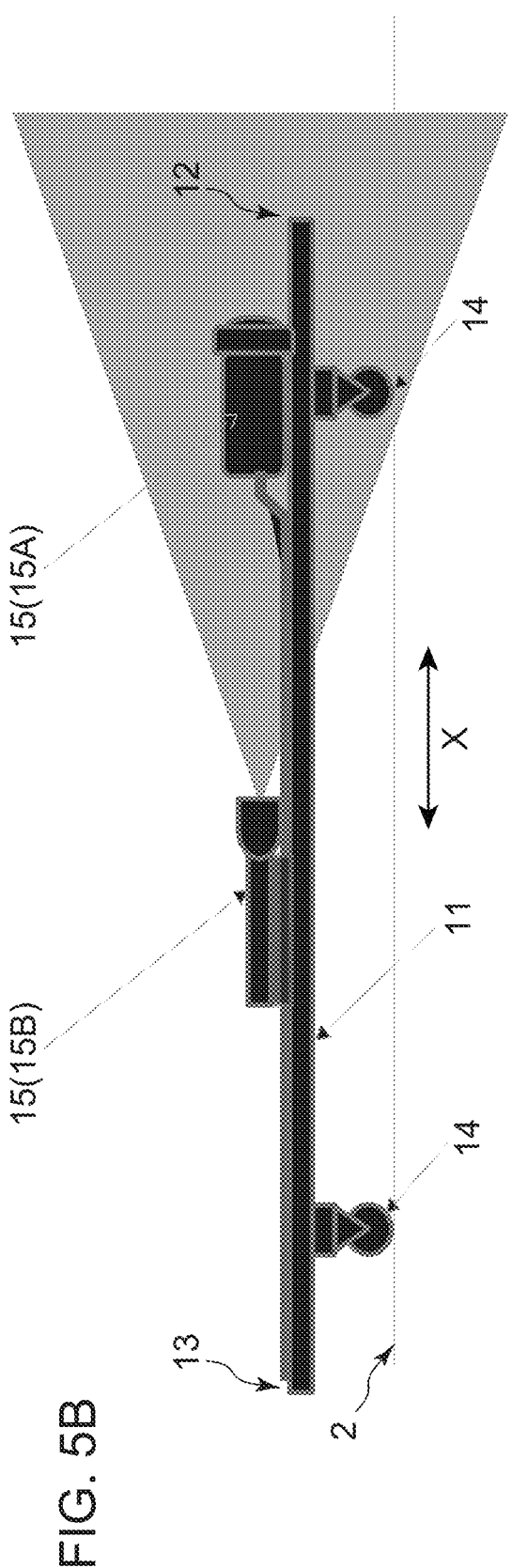

FIG. 1 is a schematic view illustrating a wind turbine according to one embodiment. FIG. 2 is a perspective view illustrating an entire wind turbine blade according to one embodiment. FIG. 3 is a flowchart illustrating a method of repairing or reinforcing a wind turbine blade, or attaching an accessory part to the wind turbine blade according to one embodiment.

As illustrated in FIG. 1, a wind turbine power generation facility according to at least some embodiments of the disclosure (hereinafter, referred to as a wind turbine 1) includes: a rotor 4 including a plurality of (three in the example illustrated in FIG. 1) wind turbine blades 2 and a hub 3 to which the wind turbine blades 2 are attached; a nacelle 5 that rotatably supports the rotor 4 via a main shaft and a main bearing (not illustrated); a tower 6 supporting the nacelle 5 yaw-rotatably; and a base 7 on which the tower 6 is installed. The number of wind turbine blades 2 may be more than or less than three.

As illustrated in FIG. 2, in some embodiments, the wind turbine blades 2 each include a blade main body 2C extending from a blade root portion 2A to a blade tip portion 2B, along a longitudinal direction (blade spanwise direction X).

The blade main body 2C includes: the blade root portion 2A attached to the hub 3 of the wind turbine 1; the blade tip portion 2B that is a portion farthest from the hub 3; and an airfoil portion 2D extending between the blade root portion 2A and the blade tip portion 2B along the blade spanwise direction X. The blade main body 2C further includes a leading edge 8A and a trailing edge 8B both extending from the blade root portion 2A to the blade tip portion 2B. The blade main body 2C has an outer shape defined by a front surface 10 (suction surface) and a back surface 12 (pressure surface) opposite to the front surface 10.

The "blade spanwise direction" as used in this specification is a direction between the blade root portion 2A and the blade tip portion 2B, and a "chordwise direction (blade chordwise direction)" is a direction along a line (chord) between the leading edge 8A and the trailing edge 8B of the blade main body 2C. The "blade root portion" is a cylindrical portion of the wind turbine blade 2, with a substantially circular cross-sectional shape. The blade root portion is within a range of 5 m in the blade spanwise direction from a blade-root-side end surface of the blade main body 2C of the wind turbine blade 2 (typically within a range of 1 to 3 m from the end surface).

As in a non-limiting example illustrated in FIG. 3, a method of inspecting an interior of the wind turbine blade 2 according to at least one embodiment is a method of inspecting the wind turbine blade 2 and includes the steps of: placing, in the wind turbine blade 2, an inspection unit 10 including a support frame 11, at least one wheel 14 rotatably provided to the support frame 11, and inspection equipment 15 attached to a front portion of the support frame 11 in a traveling direction (step S10); and conveying the inspection unit from the blade root portion 2A toward the blade tip portion 2B of the wind turbine blade 2 (step S20).

The wheel 14 only needs to be provided as a single wheel to each support frame 11. For example, the wheel 14 may be provided to a front portion, a back portion, or a portion between the front and the back portions of the support frame 11 in the traveling direction. A plurality of wheels 14 may be provided to each of the front portion, the back portion, or a portion between the front and the back portions of the support frame 11, where the wheels 14 are provided.

For example, the support frame 11 may have a plate shape, a cylindrical shape, a prismatic shape, or the like, and may be a bar-shaped member elongated along the traveling direction.

The conveying step S20 includes connecting at least one extension bar 21 to a back end portion 13 of the inspection unit 10, and sending the inspection unit 10 by pushing the extension bar 21 toward the blade tip portion 2B.

The inspection equipment 15 may be one piece of equipment provided at least on a front-most portion of the inspection unit 10, that is, a front end portion 12 of the support frame 11, or may be provided to at least one extension bar 21 as appropriate.

Examples of inspection performed with the inspection equipment 15 may include capturing images with an image capturing device (camera) 15A, and further include a hammering test using a hammering device (not illustrated).

In the method described above, the inspection unit 10 is placed in the wind turbine blade 2. The extension bar 21 is connected to the back end portion 13 of the inspection unit 10 and is pushed toward the blade tip portion 2B. Thus, the inspection unit 10 with the wheel 14 is sent toward the blade tip portion 2B. In this process, the extension bar 21 may be additionally connected in accordance with a blade length L, so that the inspection unit 10 can be conveyed to the blade tip portion 2B. Thus, the inspection unit 10 can be conveyed to the blade tip portion 2B, where the operator cannot enter, in the wind turbine blade 2 laid on the ground or an ocean (see FIG. 2), or attached to the wind turbine 1 while being horizontally or substantially horizontally arranged (see FIG. 1). All things considered, risk of an operator or an object falling down in the wind turbine blade 2 can be avoided for example, so that the interior of the wind turbine blade 2 can be safely inspected.

Figure 6A:
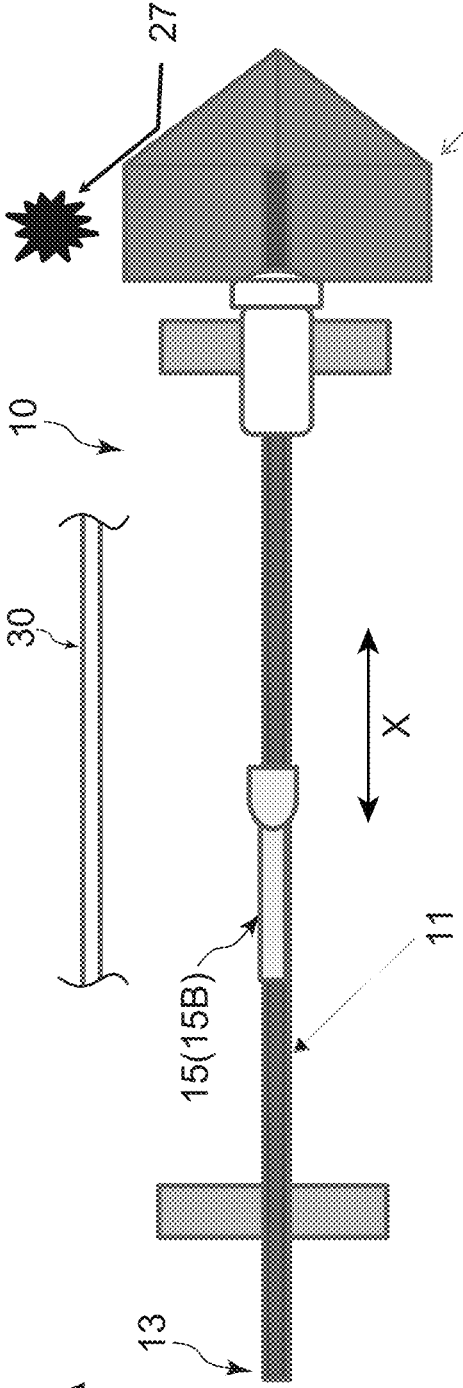
FIGS. 6A and 6B are each a schematic view illustrating an inspection unit according to one embodiment.
Figure 6B:
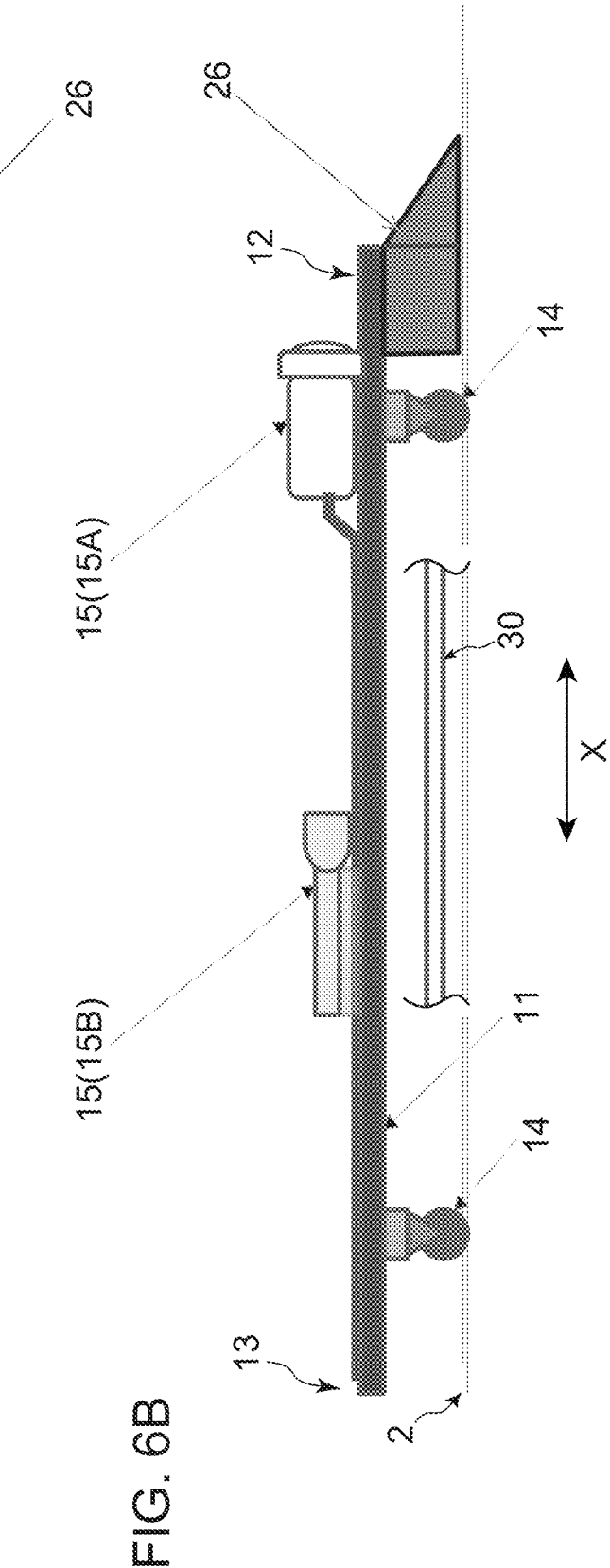
Figure 7A:
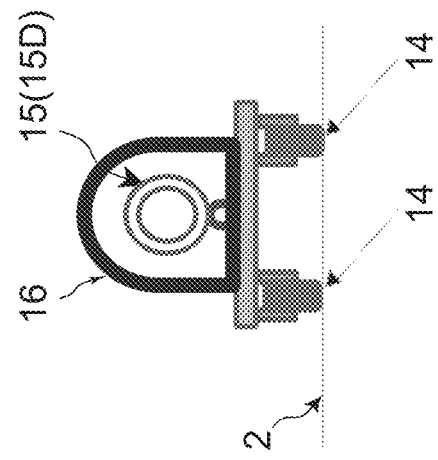
FIGS. 7A and 7B are each a schematic view illustrating an inspection unit according to another embodiment.
Figure 7B:
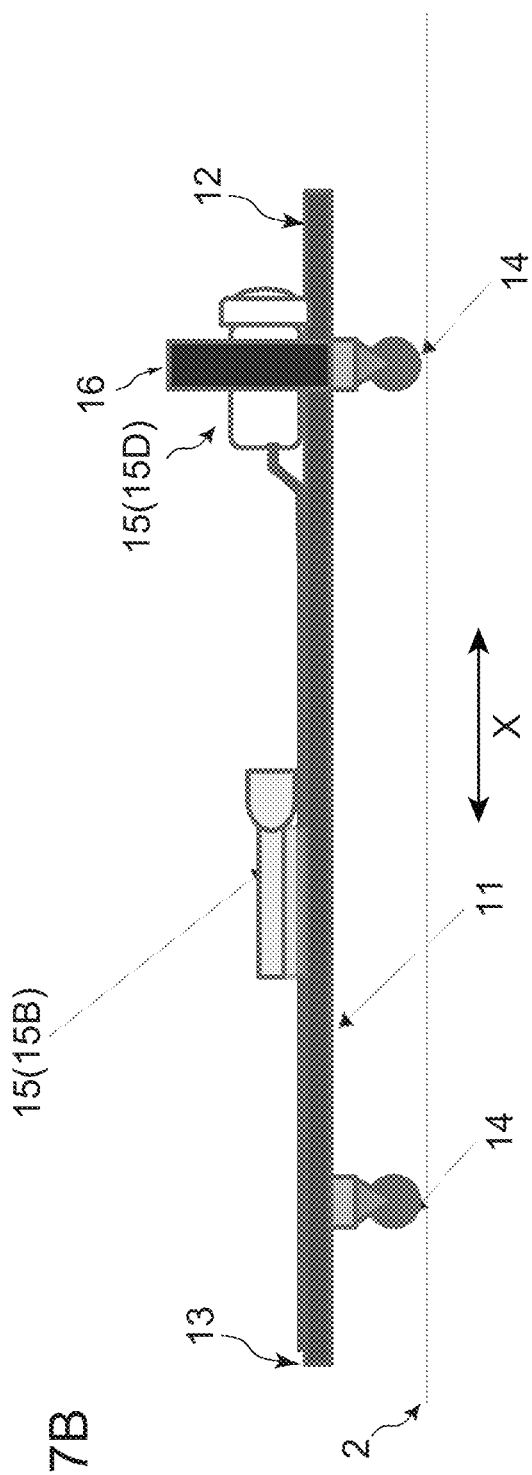

Examples of inspection targets in the wind turbine blade 2 include: a structural member 32 (see FIG. 9) on the inner surface of the wind turbine blade 2; a conducting down conductor 30 (see FIGS. 6A and 6B) on the inner surface of the wind turbine blade 2 along the blade spanwise direction X; and a foreign object 27 (see FIGS. 6A and 6B) that has entered the interior of the wind turbine blade 2.

In some embodiments, the above-described method may further include a step of maintaining an azimuth angle of the wind turbine blade 2, attached to the wind turbine 1, to be within ±30° relative to a horizontal direction (step S1), and the step S10 of placing the inspection unit 10 in the wind turbine blade 2 and the conveying step S20 may be performed on the wind turbine blade 2 attached to the wind turbine 1 with the azimuth angle maintained in the state in the maintaining step S1 (see FIG. 1 and FIG. 4, for example).

In the method described above, the azimuth angle of the wind turbine blade 2 in a state of being attached to the wind turbine 1 is maintained to be within a range of ±30° relative to the horizontal direction, that is, 90°±30° or 270°±30°. Thus, the interior of the wind turbine blade 2 in the state of being attached to the wind turbine 1 to be maintained at an angle enabling an operator to move in the wind turbine blade 2 generally safely can be inspected. Thus, the wind turbine blade 2 needs not to be detached for the inspection, whereby an inspection cost can be reduced and the work period can be shortened.

The wind turbine blade 2 can have a pitch angle appropriately set to be at a full feather pitch angle, a full fine pitch angle, or any intermediate position between these.

In some embodiments, in any of the methods described above, the conveying step S20 may include coupling a front end portion 22 of an extension bar 21 to a back end portion of the inspection unit 10 that has been sent or to a back end portion 23 of another of the extension bars 21 that is a rearmost extension bar.

In the method described above, the inspection unit 10 is conveyed toward the blade tip portion by arranging the inspection unit at the forefront, that is, on the blade tip portion 2B side, and coupling the extension bar 21 to the back end portion 13, that is, the blade root portion 2A side of the inspection unit 10, or by coupling the front end portion 22 of the additional extension bar 21 to the back end portion 23 of another of the extension bars 21 additionally coupled that is a rearmost extension bar 21. With the extension bar 21 additionally coupled in this manner, the effect described in any of the above-described embodiments can be obtained with a simple configuration.

In some embodiments, in any one of the methods described above, the extension bar 21 may be configured to be extendable in a longitudinal direction, and the conveying step S20 may include extending the extension bar 21 in the longitudinal direction.

With the method described above, the extendable extension bar 21 is used that can be contracted to be more easily conveyed for inspecting the interior of the wind turbine blade 2, for example, so that a larger number of extension bars 21 can be conveyed at once. Furthermore, the extension bar 21 in the extended state may be coupled, so that the number of extension bars 21 required for sending the inspection unit 10 can be reduced. Furthermore, a smaller number of extension bars 21 can be more easily conveyed for inspection with only a limited space available around the blade root portion 2A, compared with a case where non-extendable extension bars 21 are used. Thus, higher operability can be achieved.

In some embodiments, the method according to any of the embodiments described above may further include the steps of: carrying the inspection unit 10 to an interior of the hub 3 to which the wind turbine blade 2 is attached (step S2), and sending the inspection unit 10 from the interior of the hub 3 to the interior of the wind turbine blade 2 (step S3) (see FIG. 4, for example).

The inspection according to the disclosure may include an operation performed by an operator inside the hub 3 (around an entrance near the blade root portion 2A).

With the method described above, the interior of the wind turbine blade 2 in a state of being attached to the hub 3 of the wind turbine 1 is inspected with the inspection unit 10 carried to the interior of the hub 3 on the blade root portion 2A side, and then sent from the interior of the hub 3 to the interior of the wind turbine blade 2. Thus, the effect described in any of the embodiments described above can be achieved for the operation in a limited space within the hub 3 for inspecting the interior of the wind turbine blade 2 in the state of being attached to the wind turbine 1.

Figure 10:
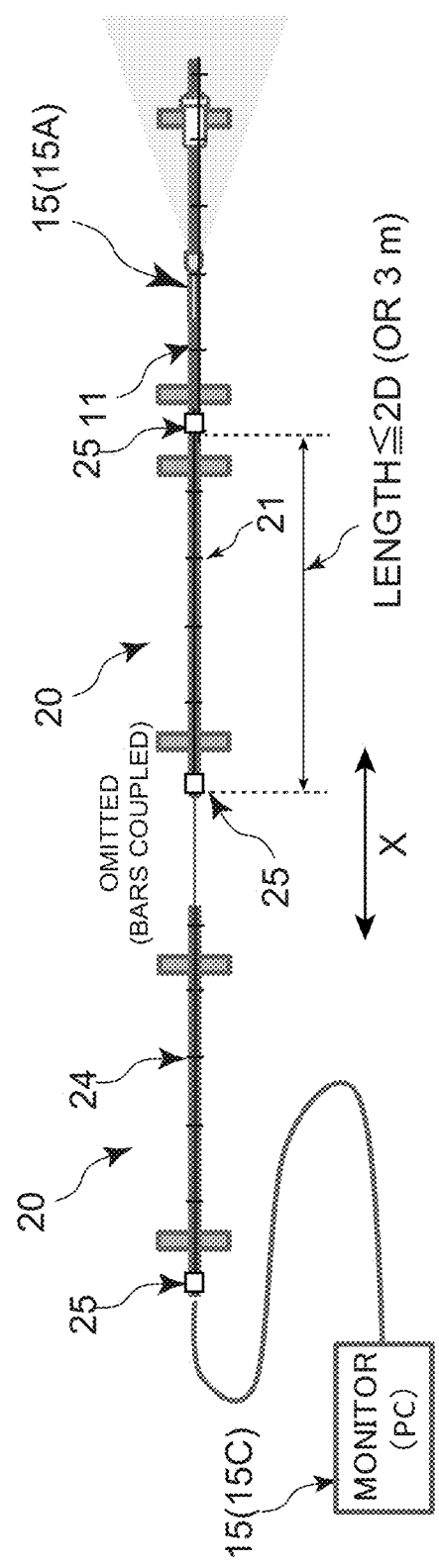
FIG. 10 is a schematic view illustrating an inspection unit according to another embodiment.

In some embodiments, in the method according to any of the embodiments described above, the extension bars 21 may be each formed to have a length in a longitudinal direction, in a shortest state, of 3 m or less, or of twice a diameter D of the blade root portion 2A or less (see FIG. 2 and FIG. 10, for example).

In the method described above, the extension bars 21 are each formed to have a length in a longitudinal direction, in a shortest state, of 3 m or less, or of twice the diameter D of the blade root portion 2A or less. Thus, the extension bars 21 with a length suitable to be conveyed can be used for the inspection, regardless of the blade length L of the wind turbine blade 2 that is the inspection target. Furthermore, the extension bars 21 can be smoothly carried to the interior of the hub 3 temporarily when required, for inspecting the interior of the wind turbine blade 2 in the state of being attached to the wind turbine 1, for example.

In some embodiments, in the method according to any of the embodiments described above, the inspection equipment 15 may include an image capturing device 15A capable of capturing an image of the interior of the wind turbine blade 2.

With the method described above, an image of the interior of the wind turbine blade 2 can be captured with the image capturing device 15A serving as the inspection equipment 15. Thus, visual information about the interior of the wind turbine blade 2 can be obtained to achieve more accurate inspection. For example, an image capturing device or the like featuring a wider angle of view than fiber scopes or the like may be employed as the image capturing device, so that a clearer image can be obtained to achieve even more accurate inspection.

In some embodiments, in the method according to any of the embodiments described above, the inspection equipment 15 may include an illumination device 15B capable of irradiating at least a front side in the traveling direction.

With the method described above, at least the front side in the traveling direction can be irradiated by using the illumination device 15B serving as the inspection equipment 15. Thus, for example, operability and accuracy can be improved for visual inspection performed by the operator within his or her visually recognizable range. Furthermore, for example, the image capturing device 15A and the like serving as the inspection unit 10 can also be used in this configuration to capture an even clearer image with the image capturing device 15A, whereby the inspection accuracy can be further improved.

In some embodiments, in the method according to any of the embodiments described above, the inspection unit 10 may further include a display unit 15C that displays an inspection result obtained by the inspection equipment 15, and the method may further include a step of displaying the inspection result on the display unit 15C (step S30).

In the method described above, the inspection result obtained by the inspection equipment 15 is displayed on the display unit 15C. Thus, the operator on site can recognize the inspection result in real time, whereby the interior of the wind turbine blade 2 can be inspected with higher operability and accuracy.

In some embodiments, in the method according to any of the embodiments described above, the extension bars 21 may be each provided with a graduation 24 indicating a distance between the back end portion 23 of the extension bar 21 and a tip of the inspection unit 10, or an index 25 indicating a coupling number of the extension bars 21, starting from the inspection unit 10, and the conveying step S20 may include conveying the inspection unit 10 while checking the graduation 24 or the index 25 (see FIG. 10, for example).

With the method described above, the inspection unit 10 can be conveyed toward the blade tip portion 2B while checking the graduation 24 or the index 25 provided to the extension bars 21. Thus, the operator can easily recognize a position of a portion in the wind turbine blade 2 where an abnormality has been found, in the blade spanwise direction X or relative to the entire wind turbine blade 2. The position thus recognized enables the operability of the inspection to be improved, and can contribute to decision making for taking appropriate measures for performing the repairing and the like on the wind turbine blade 2, for example.

In some embodiments, the method according to any of the embodiments described above may further include a step of performing a light work involved in an inspection, by using an instrument 26 provided to the front end portion 12 of the inspection unit 10 (step S40) (see FIG. 4, for example).

With the method described above, the light work involved in the inspection can be performed with the instrument 26 provided to the front end portion 12 of the inspection unit 10. Examples of the light work may include removal of an obstacle, chemical spraying, light/sound emission, and cutting or attaching a member. With this configuration, the inspection can be performed through an operation with a higher degree of freedom.

An inspection unit 10 for a wind turbine blade according to at least one embodiment of the disclosure includes: an inspection unit 10 including a support frame 11 that is long in a traveling direction, wheels 14 rotatably provided to front and back portions of the support frame 11, and inspection equipment 15 attached to the front portion of the support frame 11 in the traveling direction; and at least one extension unit 20 including an extension bar 21 connected to a back end portion 13 of the inspection unit 10 (see FIG. 10, for example).

In the above-described configuration, as described above, the inspection unit 10 is placed in the wind turbine blade 2. The extension bar 21 is connected to the back end portion 13 of the inspection unit 10, and the extension unit 20 including the extension bar 21 is pushed toward the blade tip portion 2B. Thus, the inspection unit 10 with the wheel 14 is sent toward the blade tip portion 2B. In this process, the extension bar 21 may be additionally connected in accordance with a blade length L, so that the inspection unit 10 can be conveyed to the blade tip portion 2B. Thus, the inspection unit 10 can be conveyed to the blade tip portion 2B, where the operator cannot enter, in the wind turbine blade 2 laid on the ground or an ocean or attached to the wind turbine while being horizontally or substantially horizontally arranged. All things considered, risk of an operator or an object falling down in the wind turbine blade 2 can be avoided for example, so that the interior of the wind turbine blade 2 can be safely inspected.

In some embodiments, in the configuration described above, the inspection unit 10 may further include a sensor 15D that is arranged in a periphery of the inspection equipment 15 and that detects contact with surroundings in at least one of a height direction or a width direction (see FIGS. 7A and 7B, FIGS. 8A and 8B, and FIG. 9, for example).

With this configuration, the sensor 15D can detect contact between the inspection unit 10 and surroundings in at least one of the height direction or the width direction. Thus, the for example, contact between the inspection unit 10 and the inner surface of the wind turbine blade 2, a structure of the wind turbine blade 2, or a foreign object and the like in the wind turbine blade 2 can be detected.

Figure 8A:
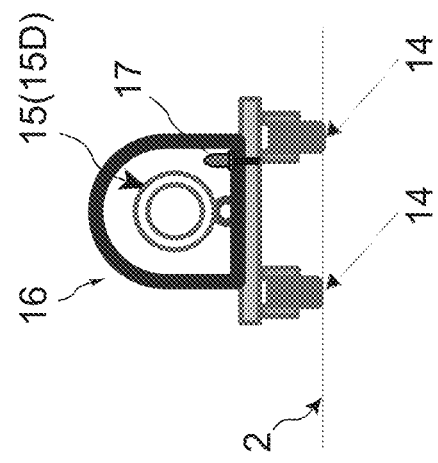
FIGS. 8A and 8B are each a schematic view illustrating an inspection unit according to another embodiment.
Figure 8B:
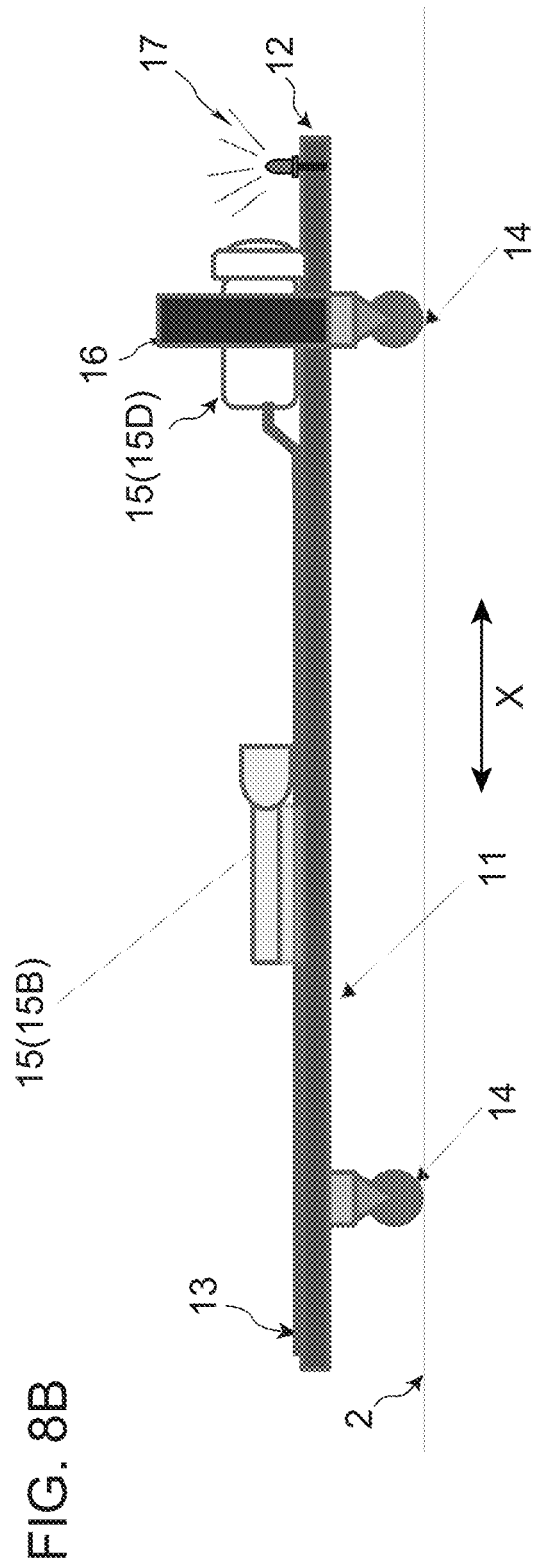
Figure 9:
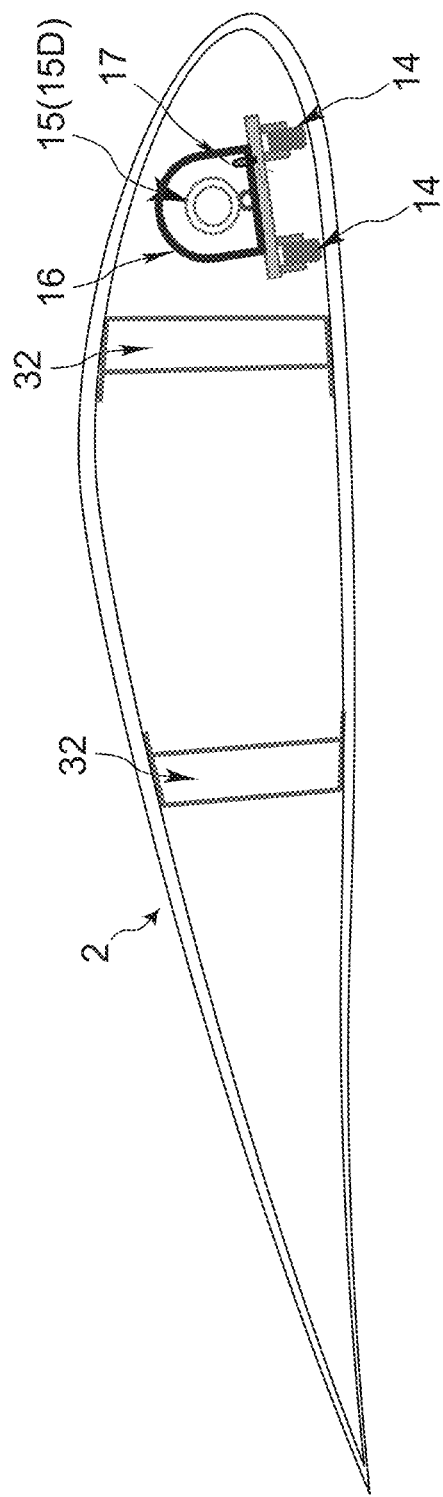
FIG. 9 is a schematic view illustrating an inspection unit according to another embodiment.

In some embodiments, in the configuration described above, the inspection unit 10 may further include a notification unit 17 that issues a notification indicating a detection result obtained by the sensor 15D (see FIGS. 8A and 8B and FIG. 9, for example).

With this configuration, the notification unit 17 issues the notification indicating the detection result obtained by the sensor 15D. Thus, the operator can recognize and record the contact between the inspection equipment 15 and the surroundings. For example, the traveling direction of the inspection unit 10 can be corrected, the inspection can be terminated in response to recognizing that the inspection unit 10 has reached a portion near the blade tip portion 2B, and other like actions can be made on the basis of the notification issued by the notification unit 17.

With at least one embodiment of the disclosure, the interior of the wind turbine blade 2 can be safely inspected.

While some embodiments of the disclosure have been described, it should be noted that the disclosure is not limited to the embodiments described above and also includes embodiments with modifications to the embodiments described above and a combination of these embodiments.

The invention claimed is:

1. A method of inspecting an interior of a wind turbine blade, the method comprising the steps of:
   placing, in the wind turbine blade, an inspection unit including a support frame, at least one wheel rotatably provided to the support frame, and an inspection equipment attached to a front portion of the support frame in a traveling direction;
   conveying the inspection unit from a blade root portion toward a blade tip portion of the wind turbine blade; and
   maintaining an azimuth angle of the wind turbine blade, attached to a wind turbine, to be within ±30° relative to a horizontal direction,
   wherein the conveying step includes connecting at least one extension bar to a back end portion of the inspection unit, and sending the inspection unit by pushing the extension bar toward the blade tip portion, and
   wherein the step of placing the inspection unit in the wind turbine blade and the conveying step are performed on the wind turbine blade attached to the wind turbine with the azimuth angle maintained in a state in the maintaining step.

2. The method of inspecting an interior of a wind turbine blade according to claim 1,
   wherein the conveying step includes coupling a front end portion of the extension bar to a back end portion of the inspection unit that has been sent or to a back end portion of another of the extension bars that is a rearmost extension bar.

3. The method of inspecting an interior of a wind turbine blade according to claim 1,
   wherein the extension bar is configured to be extendable in a longitudinal direction, and the conveying step includes extending the extension bar in the longitudinal direction.

4. The method of inspecting an interior of a wind turbine blade according to claim 1, further comprising the steps of:
   carrying the inspection unit to an interior of a hub to which the wind turbine blade is attached; and
   sending the inspection unit from the interior of the hub to the interior of the wind turbine blade.

5. The method of inspecting an interior of a wind turbine blade according to claim 1,
   wherein the extension bars are each formed to have a length in a longitudinal direction, in a shortest state, of 3 m or less, or of twice a diameter of the blade root portion or less.

6. The method of inspecting an interior of a wind turbine blade according to claim 1,
   wherein the inspection equipment includes an image capturing device capable of capturing an image of the interior of the wind turbine blade.

7. The method of inspecting an interior of a wind turbine blade according to claim 1,
   wherein the inspection equipment includes an illumination device capable of irradiating at least a front side in the traveling direction.

8. The method of inspecting an interior of a wind turbine blade according to claim 1,
   wherein the inspection unit further includes a display unit that displays an inspection result obtained by the inspection equipment, and
   the method further comprises a step of displaying the inspection result on the display unit.

9. The method of inspecting an interior of a wind turbine blade according to claim 1,
   wherein the extension bars are each provided with a graduation indicating a distance between a back end portion of the extension bar and a tip of the inspection unit, or an index indicating a coupling number of the extension bars, starting from the inspection unit, and
   the conveying step includes conveying the inspection unit while checking the graduation or the index.

10. The method of inspecting an interior of a wind turbine blade according to claim 1, further comprising a step of performing a light work involved in an inspection, by using an instrument provided to a front end portion of the inspection unit.

* * * * *